United States Patent
Heida (10) Patent No.: US 7,556,717 B2
(45) Date of Patent: Jul. 7, 2009

(54) METHOD AND DEVICE FOR EXTRACTIVE DISTILLATION

(75) Inventor: Bernd Heida, Ellerstadt (DE)

(73) Assignee: BASF Aktiengesellschaft, Ludwigshafen (DE)

(*) Notice: Subject to any disclaimer, the term of this patent is extended or adjusted under 35 U.S.C. 154(b) by 780 days.

(21) Appl. No.: 10/524,356

(22) PCT Filed: Dec. 11, 2003

(86) PCT No.: PCT/EP03/14074

§ 371 (c)(1),
(2), (4) Date: Feb. 14, 2005

(87) PCT Pub. No.: WO2004/052492

PCT Pub. Date: Jun. 24, 2004

(65) Prior Publication Data

US 2005/0199482 A1 Sep. 15, 2005

(30) Foreign Application Priority Data

Dec. 12, 2002 (DE) .............................. 102 58 160

(51) Int. Cl.
*B01D 3/40* (2006.01)
*C07C 7/08* (2006.01)

(52) U.S. Cl. .............................. 203/52; 203/27; 203/39; 203/98; 203/99; 203/DIG. 19; 585/804; 585/805; 585/807; 585/833; 585/901

(58) Field of Classification Search ............... 203/1, 203/3, 27, 39, 52, 98, 99, DIG. 8, DIG. 19; 585/804, 805, 807, 833, 901, 914
See application file for complete search history.

(56) References Cited

U.S. PATENT DOCUMENTS

| | | | |
|---|---|---|---|
| 6,514,387 B1 * | 2/2003 | Emmrich et al. | 202/153 |
| 6,550,274 B1 | 4/2003 | Agrawal | |
| 2007/0039813 A1 * | 2/2007 | Heida | 203/2 |
| 2008/0228019 A1 * | 9/2008 | Heida | 585/324 |

FOREIGN PATENT DOCUMENTS

| | | | |
|---|---|---|---|
| DE | 199 58 464 | | 3/1999 |
| DE | 10022465 | * | 5/2000 |
| DE | 100 02 806 | | 7/2001 |
| DE | 101 05 660 | | 8/2002 |
| DE | 102 33 620 | | 2/2004 |
| EP | 0 755 707 | | 1/1997 |

* cited by examiner

*Primary Examiner*—Virginia Manoharan
(74) *Attorney, Agent, or Firm*—Oblon, Spivak, McClelland, Maier & Neustadt, P.C.

(57) ABSTRACT

A process for fractionating a starting mixture of two or more components by extractive distillation using a selective solvent in a dividing wall column aligned in the longitudinal direction of the column and extending to the upper end of the column and dividing the column interior into a first region, a second region, and a lower combined column region. The starting mixture is fed into the first region, a first top stream is taken off from the first region, and a second top stream is taken off from the second region, each stream having a prescribed specification. The selective solvent is introduced in the upper part of the first region and/or in the upper part of the second region, and solvent flow into the first region and/or solvent flow into the second region are set so that each of the prescribed specifications for the top streams are met.

17 Claims, 9 Drawing Sheets

METHOD AND DEVICE FOR EXTRACTIVE DISTILLATION

The present invention relates to a process for fractionating a starting mixture of two or more components by extractive distillation in a dividing wall column, to a dividing wall column suitable for this purpose and to a use.

Extractive distillation is a known method of fractionally distilling mixtures of components which have only slight differences in their relative volatilities or which boil azeotropically. Extractive distillation is carried out with addition of a selective solvent, also referred to as extractant, which has a boiling point which is substantially higher than that of the mixture to be fractionated and increases the differences in the relative volatilities of the individual components of the mixture to be fractionated due to its selective affinity for the individual components. An important criterion for selection of a suitable selective solvent is to find an absorber which makes the separation possible with a minimum of circulating absorber phase, i.e. has a sufficiently high uptake capacity.

The use of dividing wall columns for relatively complex separation tasks, in general for mixtures of at least three components which are each to be obtained in pure form, is known. They possess a dividing wall, i.e. a flat metal sheet which is generally aligned in the longitudinal direction of the column and prevents transverse mixing of the liquid and vapor streams in the regions of the column. Compared to classical distillation columns, dividing wall columns are economically advantageous since they can perform separation tasks for which two columns are usually necessary in a single apparatus, and the capital costs and energy costs are significantly lower.

It is known that extractive distillations can be carried out in dividing wall columns.

Such a process is described, for example, in DE-C 199 58 464. As a result of a particular structural configuration of the dividing wall column in which the offtake region at the upper end of the dividing wall is closed, the temperature in this region of the column can be regulated by controlling the pressure prevailing therein. Since the pressure in the offtake region which is closed at the top can be altered from the operating pressure in the column, the pressure differences can be utilized for controlling the vapor streams entering the regions of the column divided by the dividing wall.

It is an object of the invention to provide a more economical process, in particular a process which is more advantageous in terms of energy and solvent consumption, and also a dividing wall column suitable for this purpose.

We have found that this object is achieved in terms of the process by a process for fractionating a starting mixture of two or more components by extractive distillation using a selective solvent in a dividing wall column, wherein the process is carried out in a dividing wall column having a dividing wall which is aligned in the longitudinal direction of the column and extends to the upper end of the column and divides the interior of the column into a first region, a second region and a lower combined column region, the starting mixture is fed into the first region, a first top stream is taken off from the first region and a second top stream is taken off from the second region, with each of the streams having a prescribed specification, the selective solvent is introduced in the upper part of the first region and/or in the upper part of the second region and the flow of solvent into the first region and/or the flow of solvent into the second region are set so that each of the prescribed specifications for the top streams are met.

It has surprisingly been found that a simple structural configuration of the dividing wall column, namely one in which the dividing wall extends to the upper end of the dividing wall column, enables optimum thermodynamic conditions for the respective separation task in the extractive distillation to be set independently in each of the regions of the column interior divided by the dividing wall. In particular, it is possible to introduce the optimum amount of solvent into each region, so that the uptake capacity of the solvent is utilized to the full in each of the regions and the total solvent requirement is minimized. At the same time, the energy consumption is significantly reduced compared to the "classical" dividing wall column.

Starting mixtures will generally be mixtures of hydrocarbons or of other organic components which, due to the small differences in the volatilities of at least two components or due to the formation of azeotropes, can be fractionated only by addition of a selective solvent which alters the relative volatilities.

The starting mixture is introduced in the first region of the dividing wall column, frequently in about the middle third thereof. Depending on the specific composition of the starting mixture to be fractionated, it may be possible for the component or the component mixture having the greatest volatility to be separated off from the other components of the starting mixture in a simple manner by distillation. In this case, introduction of selective solvent in the upper part of the first region is not necessary to enable a top stream consisting of a single, pure component having the greatest volatility or a set of components having the greatest volatility to be separated off.

However, the isolation of a pure component or a set of components having the greatest volatility in the first region of the dividing wall column is generally only possible with addition of a selective solvent in the upper part of the first region and thus countercurrent contact with the starting mixture to be fractionated. In this case, the selective solvent is introduced under suitable thermodynamic conditions, in general at the lowest possible temperatures, and becomes laden with the components of the starting mixture for which it has a relatively high affinity, while the component or components for which it has a lower affinity, i.e. components which are sparingly soluble in the selected solvent, remain in the vapor phase and are taken off as top stream.

The solvent laden with the components of the starting mixture for which it has a greater affinity than for the component or components which has been taken off as top stream from the first region flows in vapor form into the second region of the dividing wall column at the lower end of the dividing wall.

In the second region of the dividing wall column, it may be possible, depending on the specific composition of the starting mixture to be fractionated, to separate the components which are more readily soluble in the selective solvent by simple distillation, but it may also be the case that these can be seperated only with introduction of selective solvent in countercurrent in the upper part of the second region, i.e. by extractive distillation.

The top stream taken off from the second region can once again, as in the case of the top stream taken off from the first region, be a single, pure component or a set of components having a particular boiling range.

The top streams from the first and second regions are, as is customary, condensed in condensers at the top of the column, part of the condensate is returned as runback to the column and the remainder is taken off.

There are generally particular purity requirements, i.e. specifications, prescribed for the top streams.

Since the mixtures to be fractionated in each of the two regions of the dividing wall column always differ in terms of quantity and composition, a particular optimum amount of selective solvent will, if the fractionation is carried out by extractive distillation, always be necessary in each region in order to achieve the prescribed specifications in the top streams.

In the process of the present invention for extractive distillation in a column having a dividing wall which extends to the upper end, introduction of an optimum amount of selective solvent for the respective separation task into one or both regions, independently of one another, is possible in a simple fashion.

In one process variant, a solvent which is still laden with one or more components which are most soluble in the selective solvent is taken off at the bottom of the column. The laden solvent is subsequently freed of the components dissolved therein under suitable thermodynamic conditions in a stripping column and the purified solvent is generally recycled to the extractive distillation column.

In a preferred process variant, a gaseous stream is taken off from the lower combined column region, partly or completely condensed and all or part of the condensate is taken off and any remainder is returned as runback to the extractive distillation column. In the part of the column below this offtake point, the dissolved components are completely given off in gaseous form from the solvent.

It is also possible, depending on the separation task to be performed, to take off one or more additional side streams from each appropriate column region, in particular from the first region and/or the second region and/or the lower combined column region.

In a process variant which is particularly advantageous in energy terms, a liquid stream is taken off from one or more thermodynamically suitable stages of the extractive distillation column, partly or completely vaporized by heat transfer from the hot, degassed solvent and returned to the extractive distillation column at the same theoretical plate, or above the theoretical plate, from which the liquid stream had been taken off. This enables the overall energy consumption to be reduced considerably, typically by about 40-60%.

The present invention also provides a dividing wall column for carrying out an extractive distillation, which column has the particular structural feature of its dividing wall extending to the uppermost point of the column and thus allowing mixing of liquid and vapor streams only in the lower combined column region. The first and second regions referred to above are separated from one another by the dividing wall.

The length of the dividing wall and its position relative to the axis of the column can be varied depending on the composition of the starting mixture fed to the extractive distillation column and the prescribed specifications for the fractions to be separated off in the extractive distillation column. Thus, for example, it is possible for the dividing wall to be installed centrally or offcenter. An offcenter arrangement will frequently be advantageous, since the throughputs of liquid and vapor in the two regions are generally different.

In a preferred embodiment, backscrubbing trays for selective solvent entrained in the vapor stream, frequently from 3 to 5 trays, are provided in the first region and/or the second region of the extractive distillation column, in each case above the feed point for the selective solvent. Although there are in principle no restrictions in respect of the types of trays which can be used, trays for small liquid throughputs, in particular valve trays, bubble cap trays or Thormann trays, are particularly suitable.

The use of backscrubbing trays makes it possible to obtain top fractions which are particularly pure in respect of the residual solvent content.

The most important application area for the process of the present invention and the extractive distillation column of the present invention is petrochemicals, in particular the fractionation of $C_4$ fractions, $C_5$ fractions, the fractionation of aromatic mixtures, in particular benzene/toluene/xylene mixtures or mixtures of the xylene isomers.

The invention is illustrated below with the aid of an example and a drawing.

In the figures.

In the figures, identical reference numerals denote identical or corresponding features.

Figure 1:
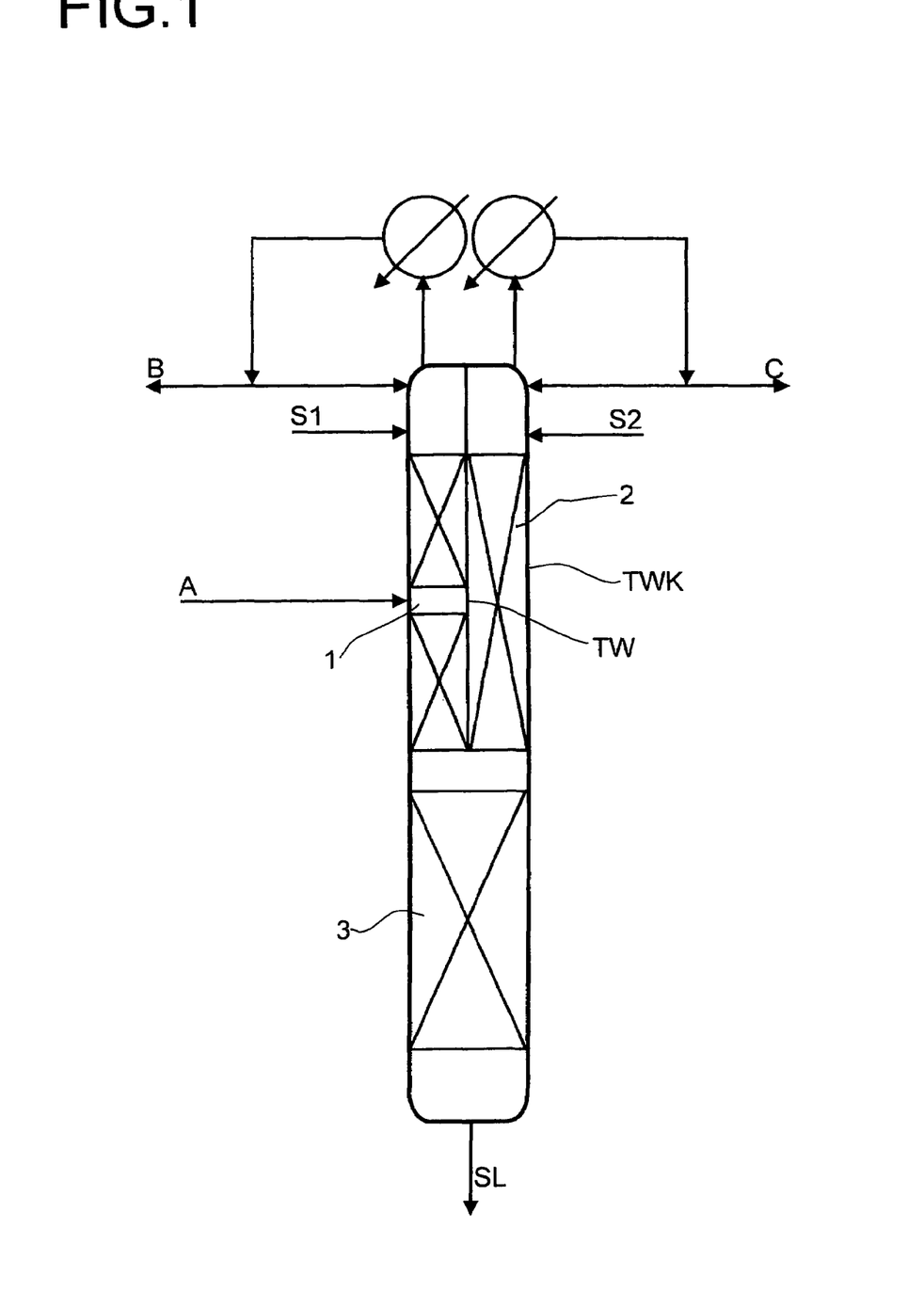
FIG. 1 schematically shows a first embodiment of an extractive distillation column according to the present invention.

The extractive distillation column shown in FIG. 1 is configured as a dividing wall column TKW having a dividing wall TW extending in the longitudinal direction of the column to the upper end of the column. The dividing wall TW divides the interior of the column into a first region 1, a second region 2 and a lower combined column region 3. The starting mixture to be fractionated A is fed into the first column region 1, approximately in the middle of this region. A first stream of the selective solvent is introduced as stream S1 in the upper part of the first region 1 and a second stream of the selected solvent is introduced as stream S2 into the upper part of the region 2. A first top stream B is taken off from the region 1, condensed in a condenser at the top of the column, part of the condensate is returned as runback to the column and the remainder is taken off. Analogously, a second top stream C is taken off from the second region 2, condensed in a condenser at the top of the column, part of the condensate is returned as runback to the second region and the remainder is taken off.

At the bottom of the column, laden selective solvent, stream SL, is taken off.

Figure 2:
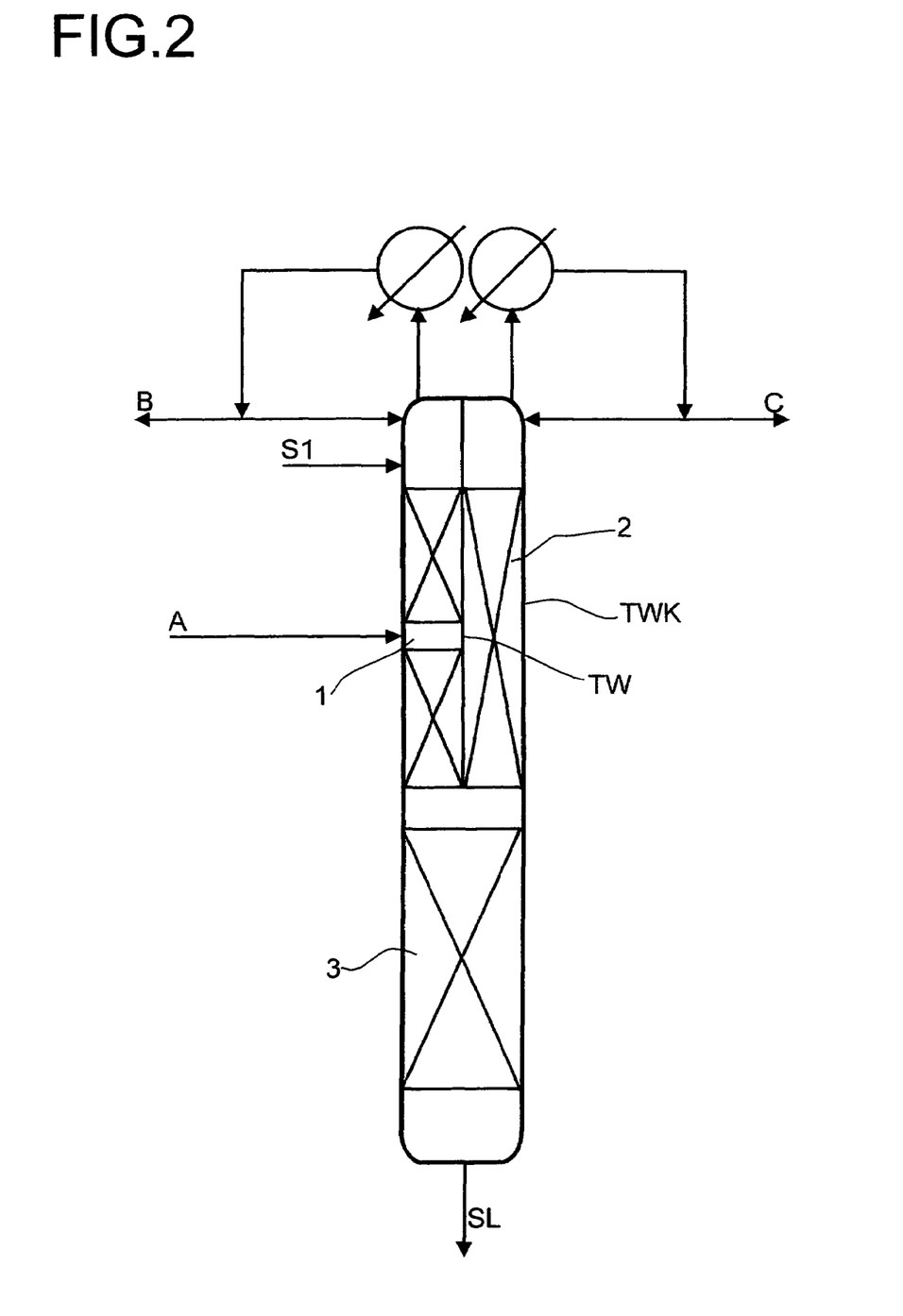
FIG. 2 shows a further preferred embodiment of an extractive distillation column according to the present invention.

The embodiment shown in FIG. 2 differs from the embodiment in FIG. 1 in that a single stream of selective solvent, stream S1, is introduced into the region 1. The fractional distillation in the region 2 occurs without addition of selective solvent.

Figure 3:
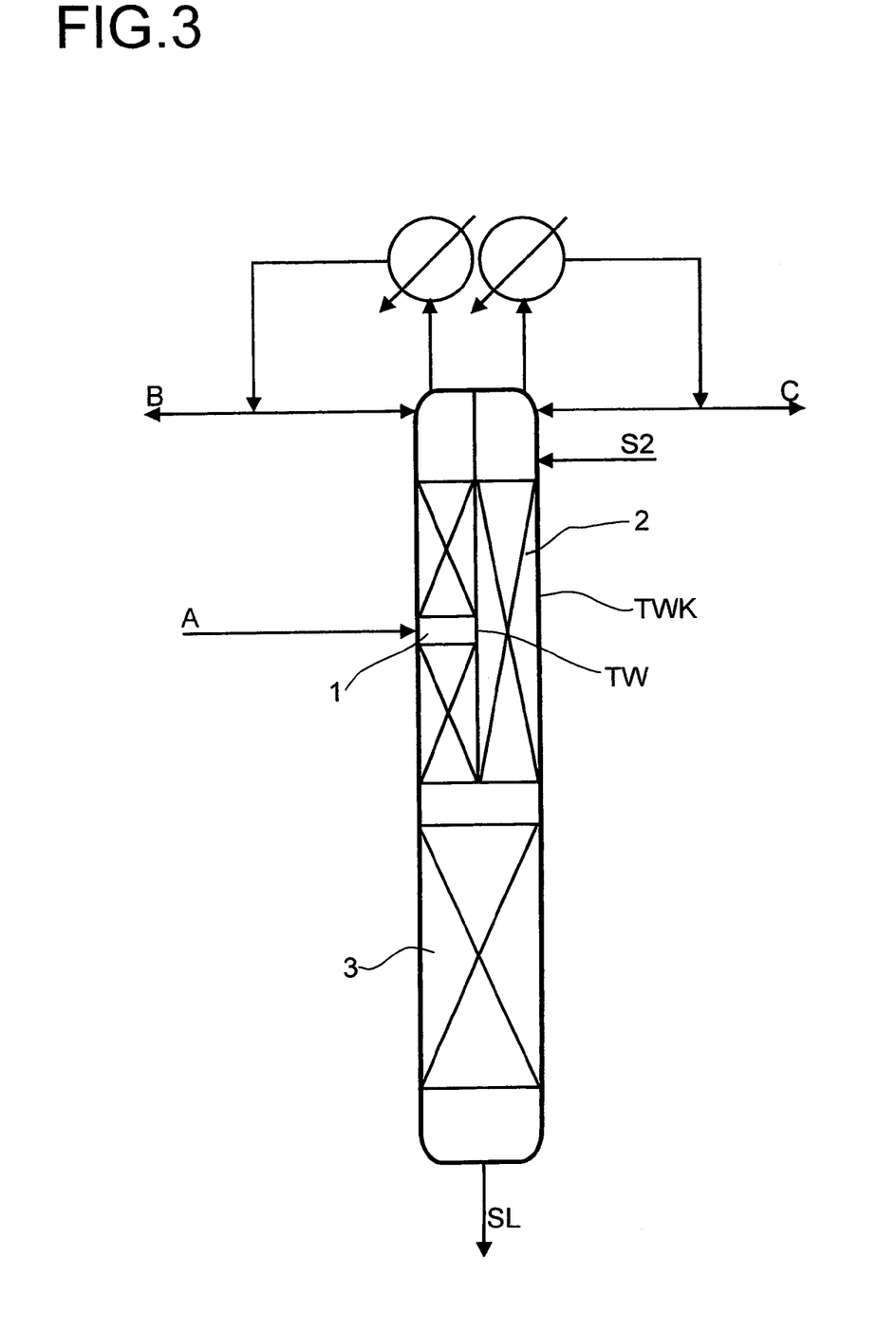
FIG. 3 shows another preferred embodiment of an extractive distillation column according to the present invention.

In the embodiment in FIG. 3, too, only a single stream of selective solvent is introduced but, unlike the case of the embodiment in FIG. 2, as stream S2 in the upper part of the region 2.

Figure 4:
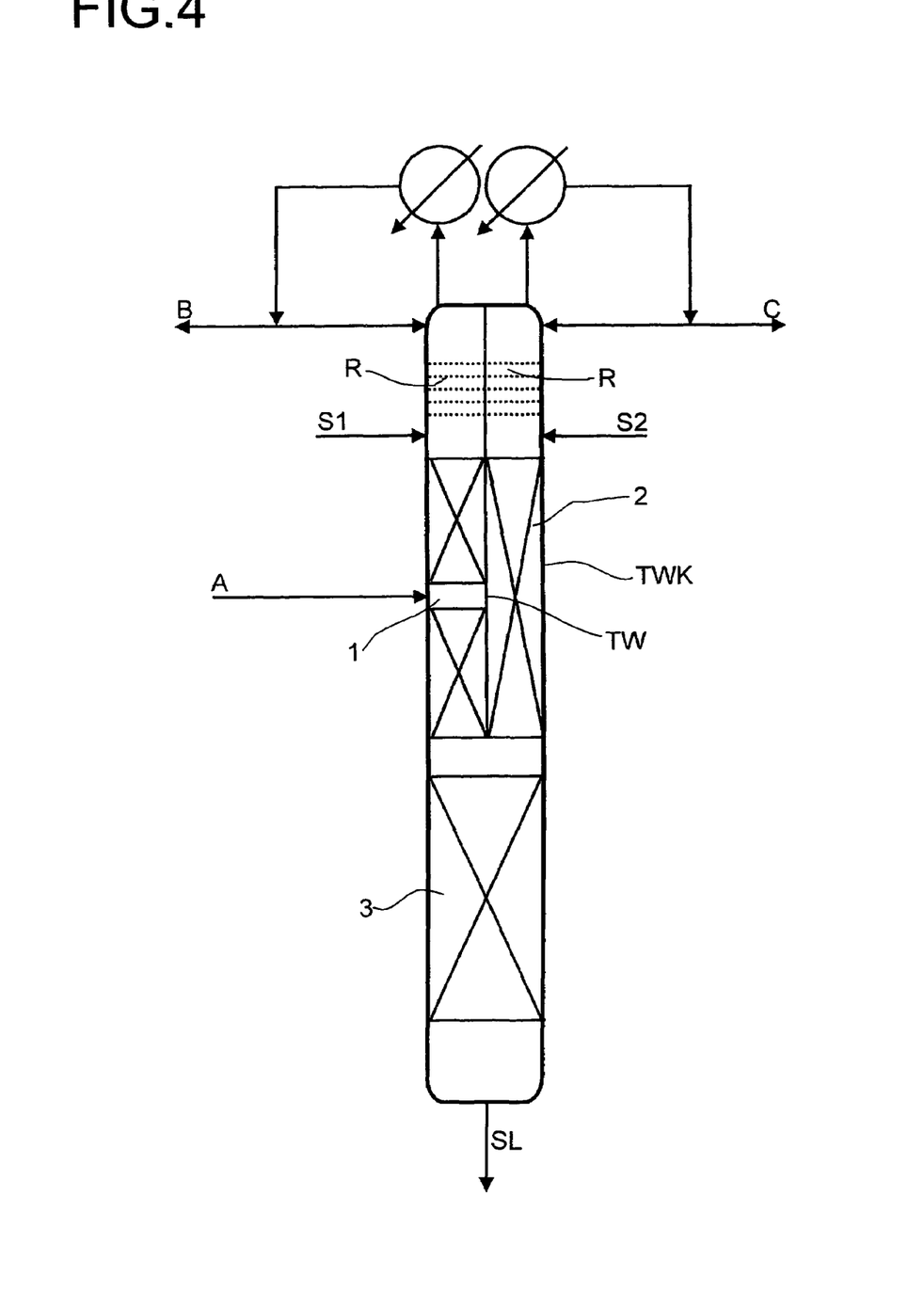
FIG. 4 shows a preferred embodiment with backscrubbing trays.

The embodiment in FIG. 4 contains, as a modification of the basic embodiment shown in FIG. 1, backscrubbing trays R which are located above the feed point for the solvent streams S1 and S2 in each of the regions 1 and 2.

Figure 5:
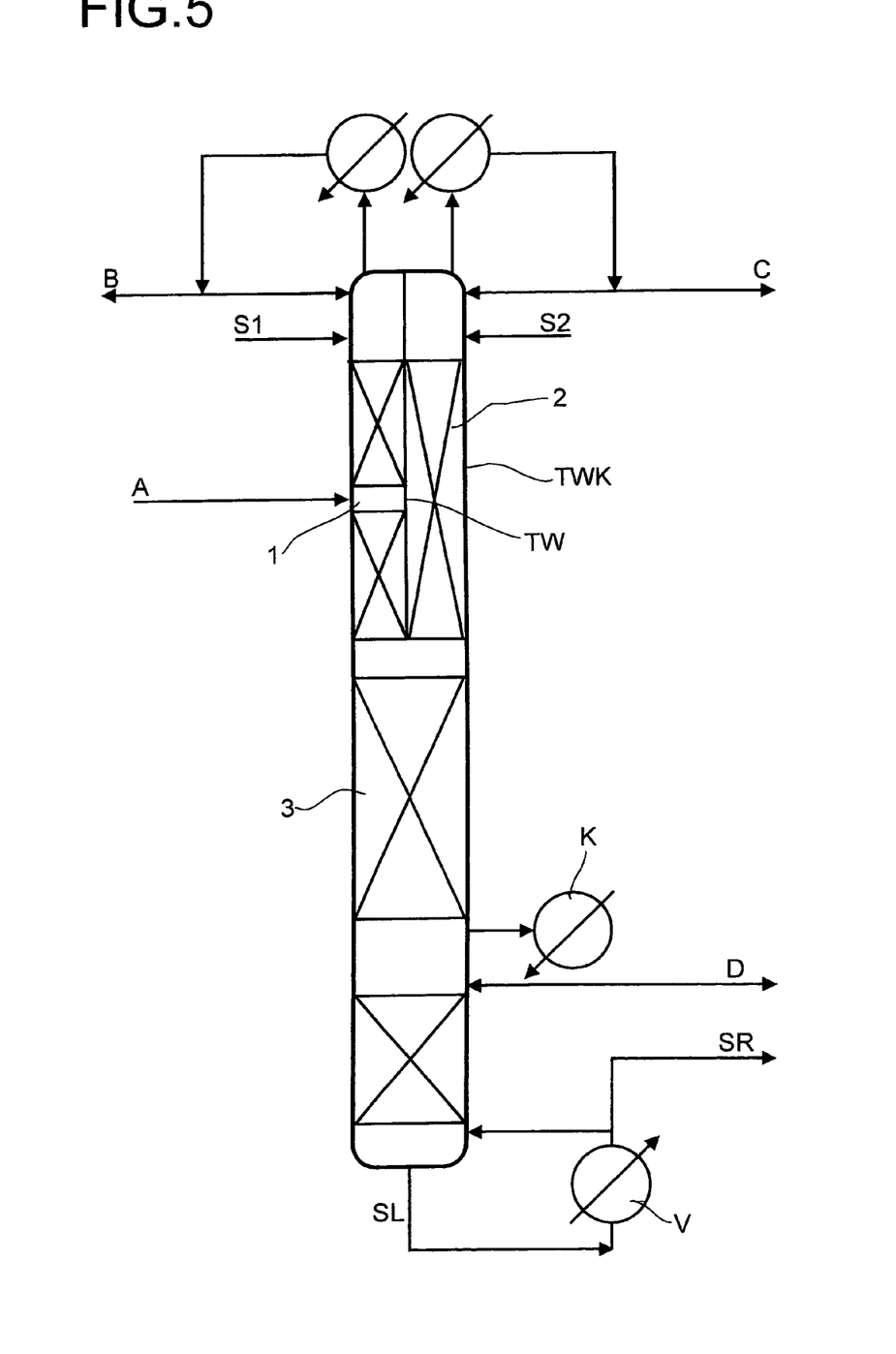
FIG. 5 shows a further embodiment with integrated solvent degassing.

In the embodiment shown in FIG. 5, a gaseous side stream is taken off from the lower combined column region 3, partially or completely condensed in a condenser, a part of the condensate is taken off as stream D and the remainder is returned as runback to the column. Below the side offtake for stream D, the laden solvent is completely degassed by introduction of heat via the bottom vaporizer V and is taken off as purified solvent, stream SR. The purified solvent is preferably recycled, after cooling in a condenser, to the extractive distillation.

Figure 6:
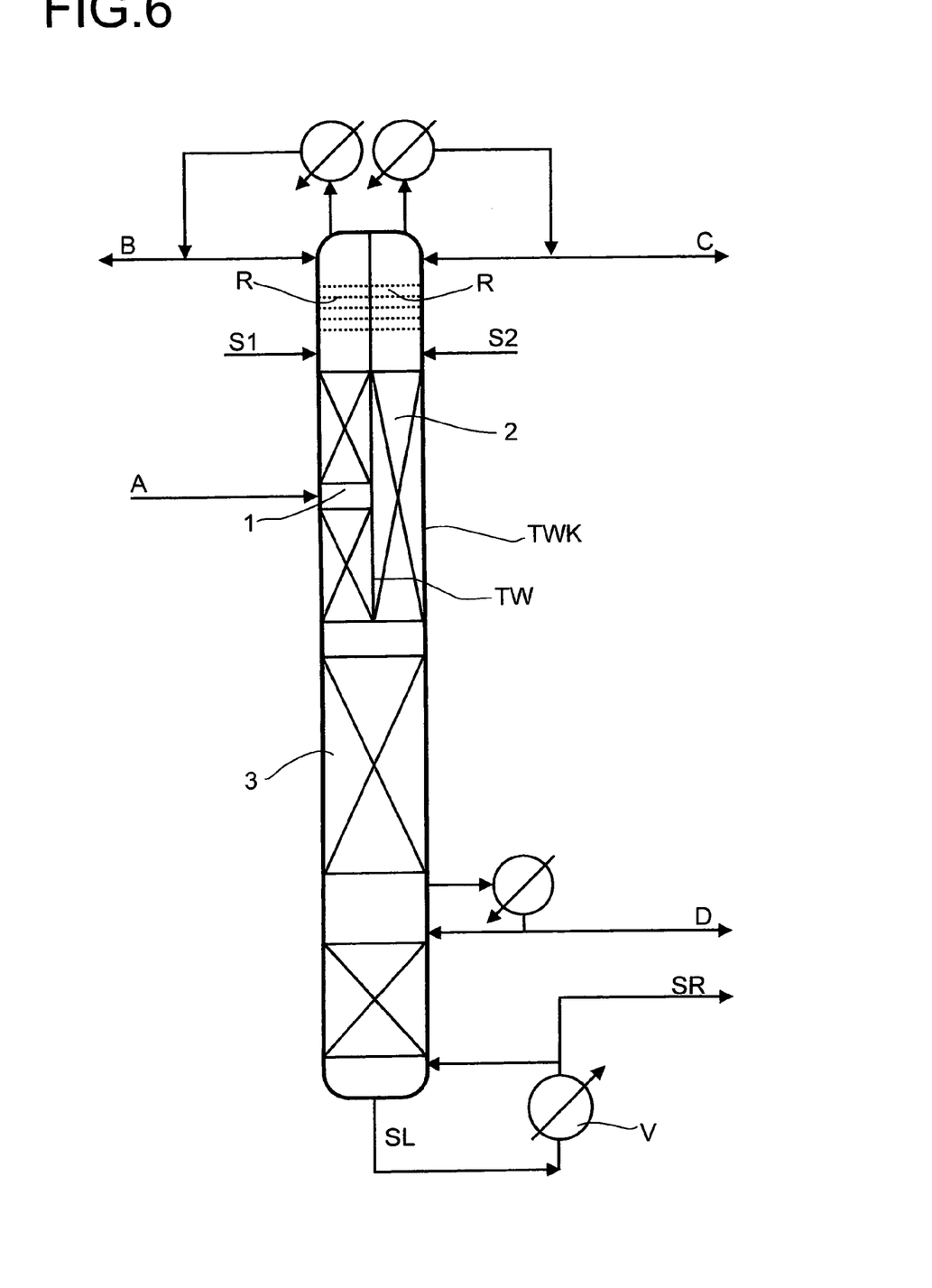
FIG. 6 shows an embodiment with backscrubbing trays and integrated solvent degassing and FIG. 7 shows an embodiment with heat integration.

The embodiment shown in FIG. 6 differs from that depicted in FIG. 5 in the provision of backscrubbing trays R in the regions 1 and 2, in each case above the feed point for the solvent streams S1 and S2.

Figure 7:
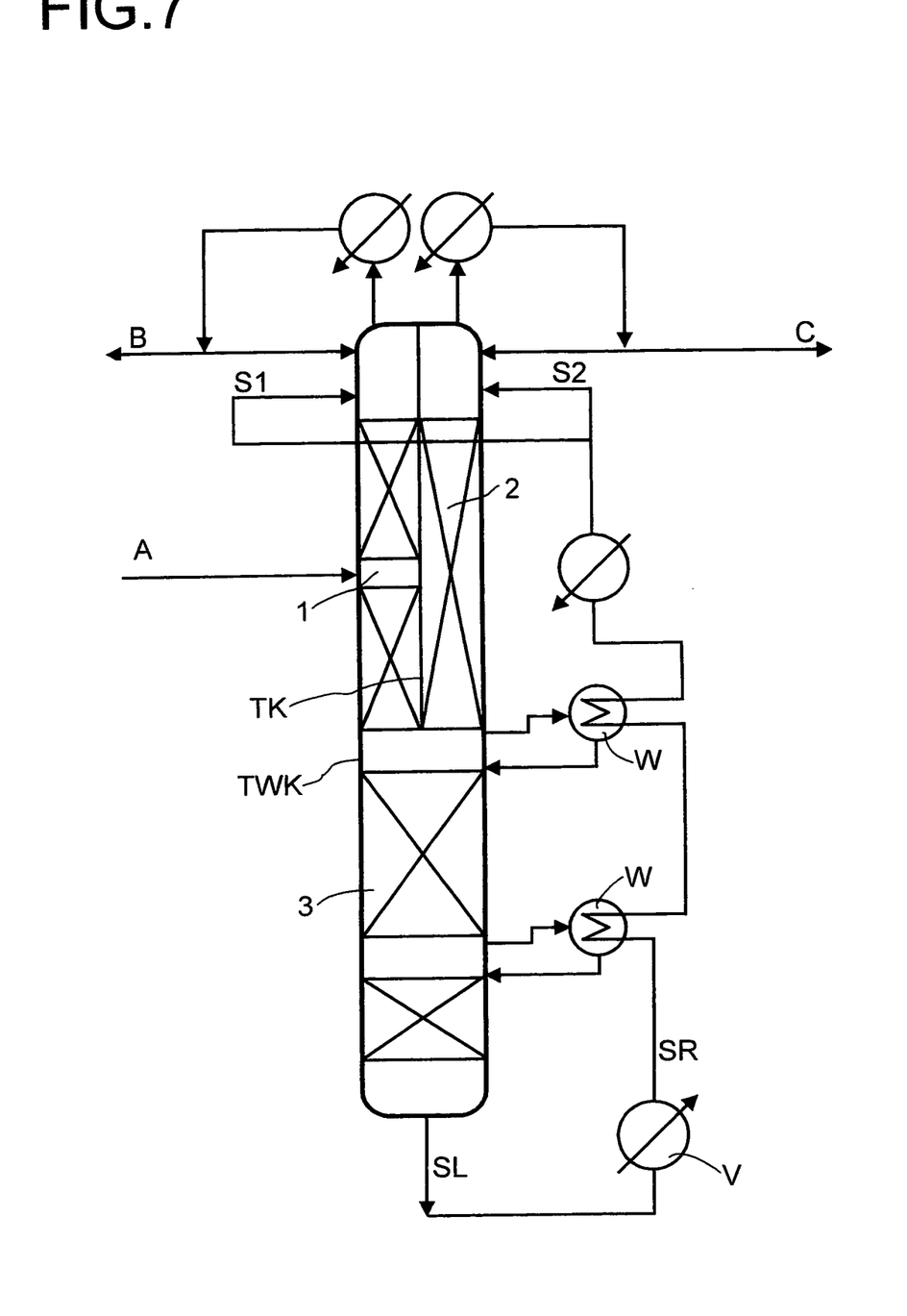

FIG. 7 shows a process variant which is particularly advantageous in energy terms and has heat integration, with hot, purified solvent, stream SR, heating liquid taken off from the extractive distillation column in heat exchangers W.

Figure 8:
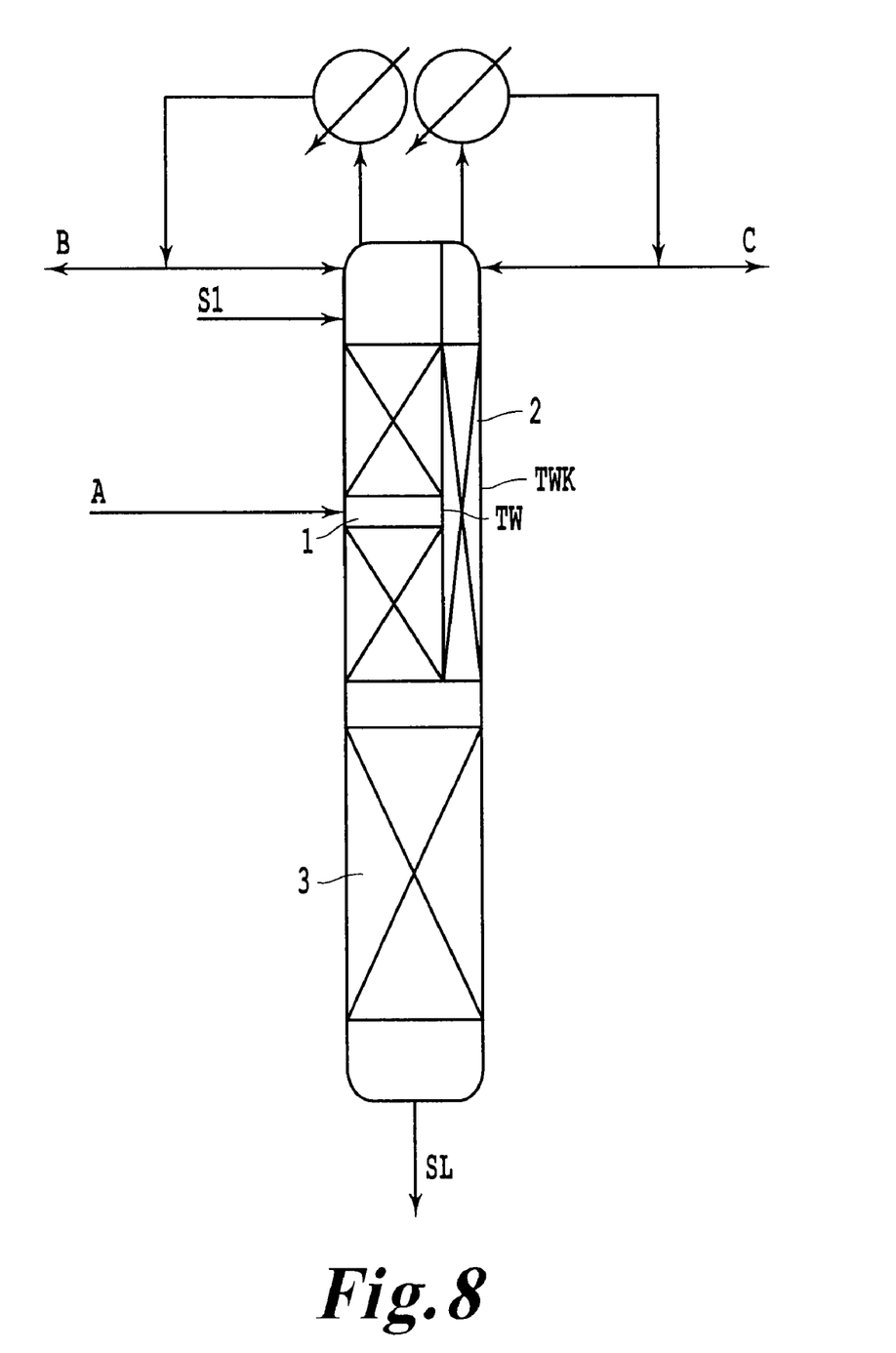
FIG. 8 shows another preferred embodiment of an extractive distillation column according to the present invention.

FIG. 8 shows a process variant wherein the dividing wall is installed offcenter in the column.

Figure 9:
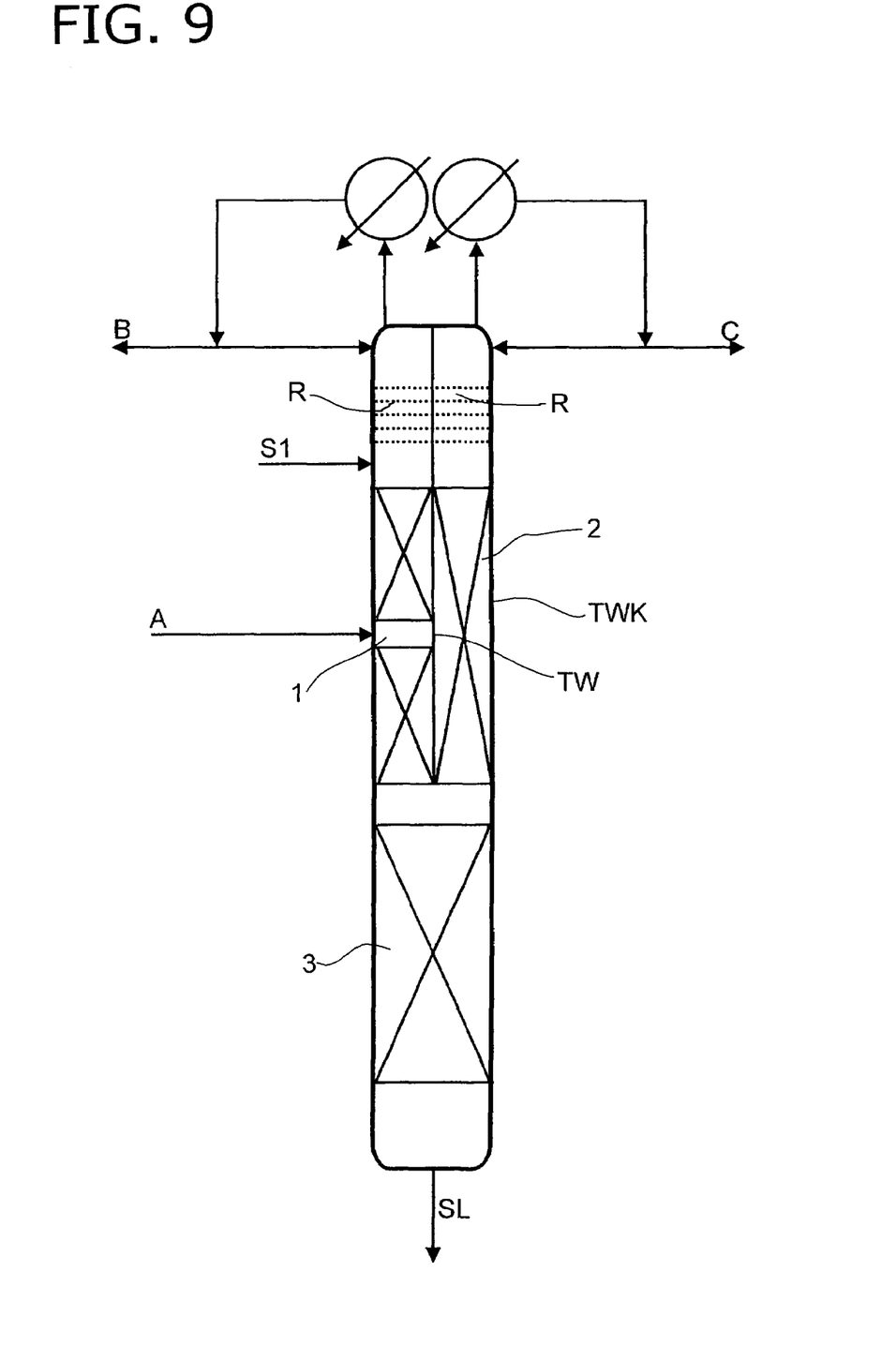
FIG. 9 shows another preferred embodiment of an extractive distillation column according to the present invention.

FIG. 9 shows a process variant wherein backscrubbing trays are provided in the region and above the feed point in which the selective solvent is introduced.

EXAMPLE

Fractionation of a $C_4$ fraction by extractive distillation.

The separation task comprises separating a $C_4$ fraction having the following composition in % by weight:

| | |
|---|---|
| propadiene | 0.03 |
| propene | 0.02 |
| propyne | 0.06 |
| n-butane | 5.74 |
| i-butane | 2.44 |
| n-butene | 13.88 |
| i-butene | 25.63 |
| trans-butene-2 | 4.44 |
| cis-butene-2 | 2.95 |
| 1,3-butadiene | 43.81 |
| 1,2-butadiene | 0.14 |
| 1-butyne | 0.13 |
| vinylacetylene | 0.73 | into a butane fraction comprising 90% by weight of butanes and a butene fraction comprising 98% by weight of butenes, in each case as top streams, and a bottom stream comprising the selective solvent together with 99% of the 1,3-butadiene and components which are more readily soluble than 1,3-butadiene.

The selective solvent used was N-methylpyrrolidone as an aqueous solution containing 8.3% by weight of water.

A feed stream of 31 250 kg/h of a $C_4$ fraction having the above composition was in each case fed into a dividing wall column having 65 theoretical plates. A dividing wall column having a conventional dividing wall, i.e. a dividing wall which does not extend to the top, was used in the comparative examples and a dividing wall extending to the upper end of the column was used in the examples according to the invention. The theoretical plates were in each case counted from the bottom upward. In the comparative examples, the dividing wall was thermodynamically optimized and was located between the 37th and 58th theoretical plate at 4 bar and between the 38th and 60th theoretical plate at 5 bar.

The critical process parameters are shown in the following table:

| | Comparison | Invention | Comparison | Invention |
|---|---|---|---|---|
| Pressure at the top [bar] | 4 | 4 | 5 | 5 |
| Vaporizer power required [kW] | 29851 | 21174 | 24570 | 20576 |
| Total amount of solvent required [kg/h] | 54860 | 373110 | 474830 | 366275 |
| Split ratio of the solvent | *1.32 | **2.71 | *1.0 | **2.80 |

*at the upper end of the dividing wall
**into the solvent streams S1/S2 in FIG. 1

The results in the table show that the vaporizer power required at a column pressure of 4 bar in the process of the present invention is 30% below that in the process using a classical dividing wall column, and at a column pressure of 5 bar is 16% lower.

In addition, the total amount of solvent required for the same separation task is 31% lower in the process according to the present invention than in a classical dividing wall column at a column pressure of 4 bar and is 23% lower at a column pressure of 5 bar. The operating costs, in particular energy costs, and the capital costs are correspondingly lower due to the lower column cross section required.

Furthermore, the classical dividing wall column has the additional disadvantage compared to the column according to the present invention having a dividing wall extending right to the top that it is less flexible in respect of changes in the working pressure: to carry out the given separation task using the above-described vaporizer power, a pressure increase of only 1 bar from 4 to 5 bar made it necessary to alter the construction of the classical dividing wall column by moving the dividing wall vertically by one theoretical plate (from the 37th to the 38th theoretical plate) and changing its length by one theoretical plate, relocating the feed point for the starting mixture to a position five theoretical plates lower down (from the 12th theoretical plate of the dividing wall region to the 7th theoretical plate of the dividing wall region) and moving the side offtake upward by one theoretical plate.

In comparison, the dividing wall column according to the present invention having a dividing wall extending right to the top required no such alteration when the working pressure was changed.

I claim:

1. A process for fractionating a starting mixture of at least two components by extractive distillation using a selective solvent in a dividing wall column, comprising
carrying out the process in a dividing wall column having a dividing wall aligned in a longitudinal direction of the column and extending to an upper end of the column and dividing an interior of the column into a first region, a second region, and a lower combined column region,
feeding the starting mixture into the first region, taking off a first top stream from the first region, and taking off a second top stream from the second region, with each of the streams having a preset composition,
introducing the selective solvent in an upper part of the first region or in an upper part of the second region, and
setting the flow of solvent into the first region or flow of solvent into the second region so that each of the preset compositions for the top streams are met, wherein at least one liquid stream or substream is taken off from the dividing wall column at at least one thermodynamically suitable theoretical plate, partly or completely vaporized by heat transfer from hot, degassed solvent stream, and returned to the dividing wall column.

2. A process as claimed in claim 1, wherein a stream of the selective solvent is introduced in the upper part of the first region.

3. A process as claimed in claim 1, wherein a stream of the selective solvent is introduced in the upper part of the second region.

4. A process as claimed in claim 1, wherein a side stream is taken off from the lower combined column region and laden solvent from the bottom of the column is degassed in a bottom vaporizer and taken off as a purified solvent stream.

5. A process as claimed in claim 4, wherein the purified solvent is recycled to the extractive distillation.

6. A process as claimed in claim 1, wherein the at least one liquid stream or substream is returned to the dividing wall column at a same theoretical plate from which the liquid stream or substream had been taken off.

7. A process as claimed in claim 1, wherein the starting mixture is a hydrocarbon mixture or an aromatic mixture.

8. A process as claimed in claim 1, wherein the starting mixture is a hydrocarbon mixture of $C_4$ fractions or $C_5$ fractions.

9. A process as claimed in claim 8, wherein the starting mixture is a hydrocarbon mixture of $C_4$ fractions.

10. A process as claimed in claim 8, wherein the starting mixture is a hydrocarbon mixture of $C_5$ fractions.

11. A process as claimed in claim 1, wherein the starting mixture is a mixture of benzene/toluene/xylene or a mixture of isomeric xylenes.

12. A process as claimed in claim 11, wherein the starting mixture is a mixture of benzene/toluene/xylene.

13. A process as claimed in claim 11, wherein the starting mixture is a mixture of isomeric xylenes.

14. A process as claimed in claim 1, wherein the dividing wall is installed centrally in the column.

15. A process as claimed in claim 1, wherein the dividing wall is installed offcenter in the column.

16. A process as claimed in claim 1, wherein backscrubbing trays are provided in the region and above the feed point in which the selective solvent is introduced.

17. A process for fractionating a starting mixture of at least two components by extractive distillation using a selective solvent in a dividing wall column, comprising carrying out the process in a dividing wall column having a dividing wall aligned in a longitudinal direction of the column and extending to an upper end of the column and dividing an interior of the column into a first region, a second region, and a lower combined column region, feeding the starting mixture into the first region, taking off a first top stream from the first region, and taking off a second top stream from the second region, with each of the streams having a preset composition, introducing the selective solvent in an upper part of the first region or in an upper part of the second region, and setting the flow of solvent into the first region or flow of solvent into the second region so that each of the preset compositions for the top streams are met, wherein a side stream is taken off from the lower combined column region and laden solvent from the bottom of the column is degassed in a bottom vaporizer and taken off as a purified solvent stream, and wherein the laden solvent is recycled to the extractive distillation.

* * * * *